(12) United States Patent
Sheu et al.

(10) Patent No.: US 10,908,155 B2
(45) Date of Patent: Feb. 2, 2021

(54) BIOLOGICAL SENSING SYSTEM

(71) Applicants: EXACT BIOCHIP CORPORATION, New Taipei (TW); NATIONAL CHIAO TUNG UNIVERSITY, Hsinchu (TW)

(72) Inventors: Jeng-Tzong Sheu, Hsinchu (TW); Chih-Wei Chen, Hsinchu (TW)

(73) Assignees: EXACT BIOCHIP CORPORATION, New Taipei (TW); NATIONAL CHIAO TUNG UNIVERSITY, Hsinchu (TW)

( * ) Notice: Subject to any disclaimer, the term of this patent is extended or adjusted under 35 U.S.C. 154(b) by 368 days.

(21) Appl. No.: 15/788,406

(22) Filed: Oct. 19, 2017

(65) Prior Publication Data

US 2018/0106796 A1 Apr. 19, 2018

Related U.S. Application Data

(60) Provisional application No. 62/409,931, filed on Oct. 19, 2016.

(51) Int. Cl.

| | |
|---|---|
| *G01N 27/00* | (2006.01) |
| *G01N 33/543* | (2006.01) |
| *H01L 29/06* | (2006.01) |
| *H01L 29/739* | (2006.01) |
| *H01L 29/423* | (2006.01) |
| *G01N 27/414* | (2006.01) |
| *H01L 29/66* | (2006.01) |
| *H01L 29/775* | (2006.01) |
| *H01L 29/45* | (2006.01) |

(52) U.S. Cl.
CPC ... *G01N 33/54373* (2013.01); *G01N 27/4145* (2013.01); *G01N 27/4146* (2013.01); *G01N 27/4148* (2013.01); *H01L 29/0673* (2013.01); *H01L 29/42392* (2013.01); *H01L 29/66356* (2013.01); *H01L 29/66439* (2013.01); *H01L 29/66772* (2013.01); *H01L 29/7391* (2013.01); *H01L 29/775* (2013.01); *H01L 29/458* (2013.01)

(58) Field of Classification Search
CPC .................. G01N 33/54373; G01N 29/022
USPC ................................ 422/82.01, 82.02
See application file for complete search history.

(56) References Cited

U.S. PATENT DOCUMENTS

2015/0017740 A1* 1/2015 Shalev ............... G01N 27/4146
436/501

* cited by examiner

*Primary Examiner* — Natalia Levkovich
(74) *Attorney, Agent, or Firm* — Rabin & Berdo, P.C.

(57) ABSTRACT

Provided is a biological sensing system, including a nanowire field-effect transistor and a sensing chip. A gate terminal of the nanowire FET surrounds a gate of a silicon nanowire or a gate of a silicon nanobelt, diameter of the silicon nanowire is less than 20 nm. A sensing electrode of the sensing chip is coupled to the gate terminal of the nanowire FET. An area ratio of an electrode area of the sensing electrode to a total sensing chip area, a thickness ratio of an oxide thickness of sensing electrode to a bulk oxide dielectric film thickness of the sensing chip and a capacitance ratio of an electrode capacitor of the sensing electrode to a gate capacitor of the silicon nanowire or a gate capacitor of the silicon nanobelt are optimized by means of an equivalent circuit so that potential coupling efficiency between sensing electrode and gate is optimized.

16 Claims, 22 Drawing Sheets

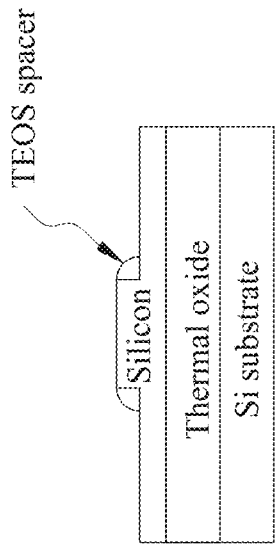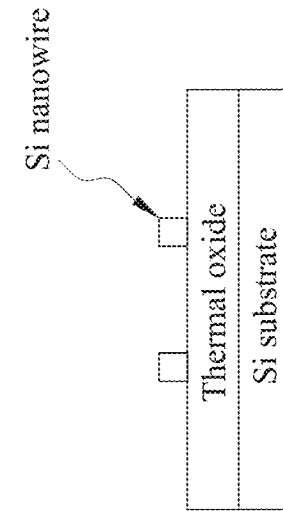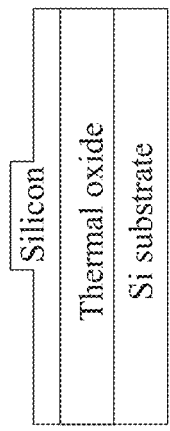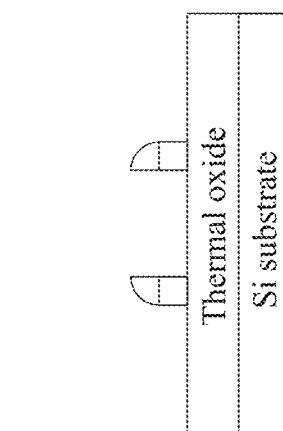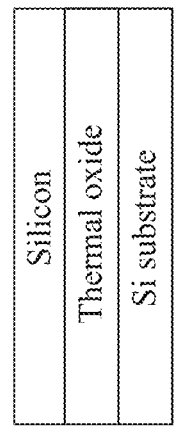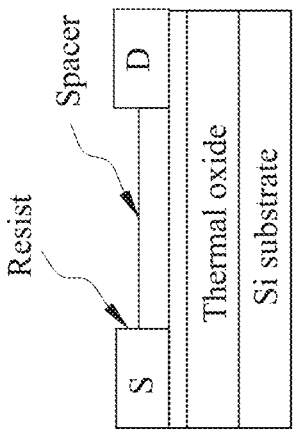

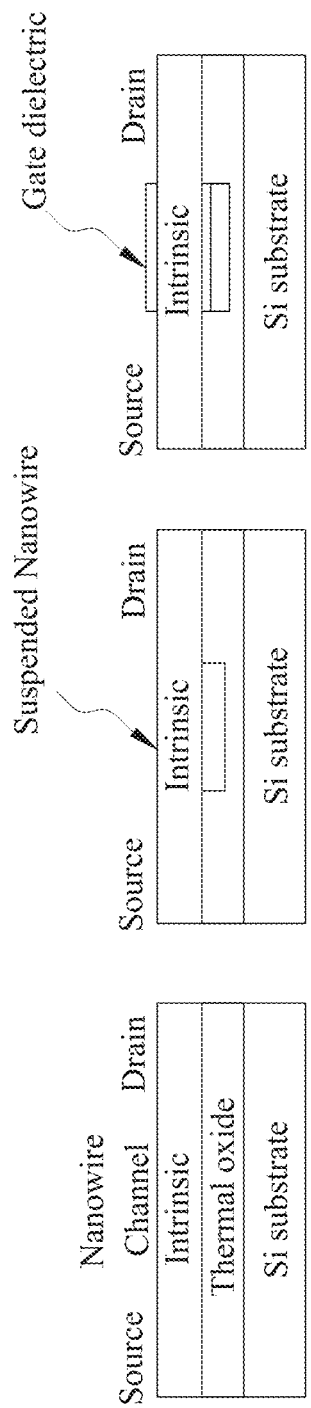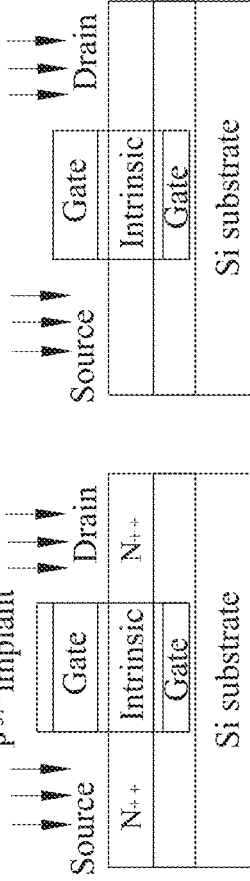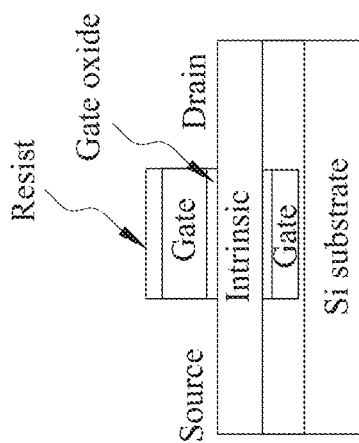

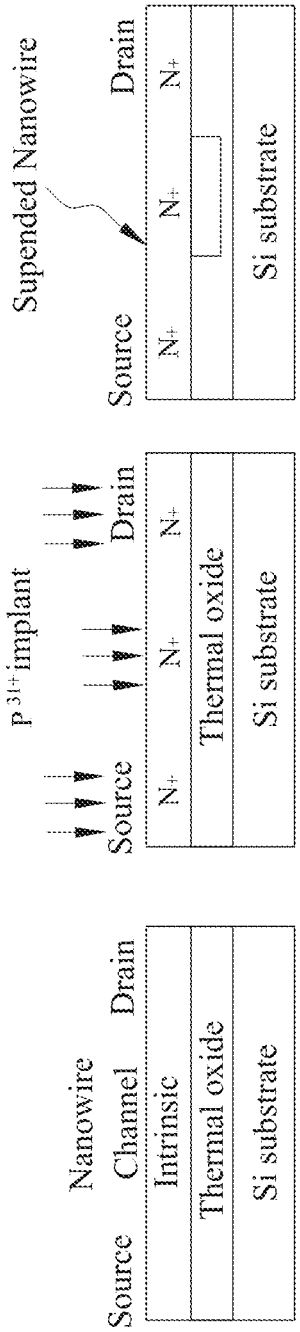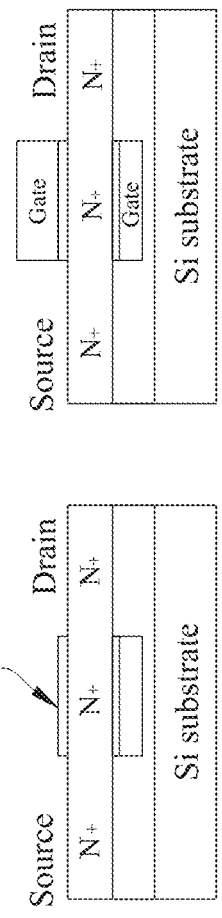

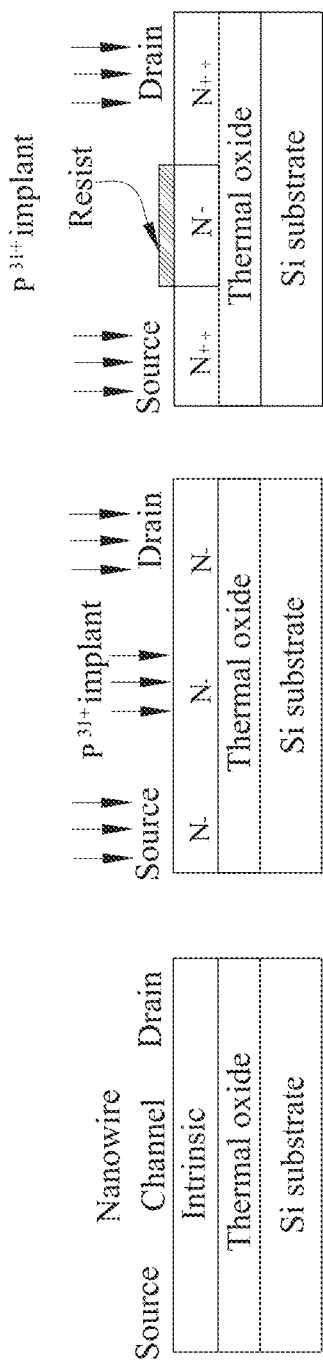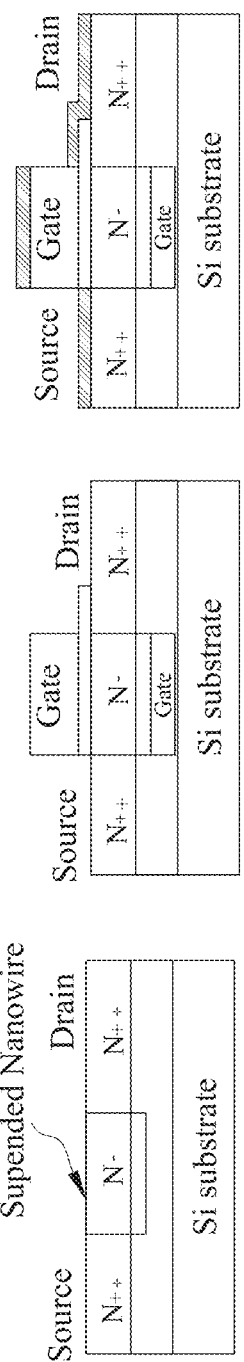
FIG. 10G
FIG. 10H
FIG. 10I
FIG. 10J
FIG. 10K
FIG. 10L
FIG. 10M

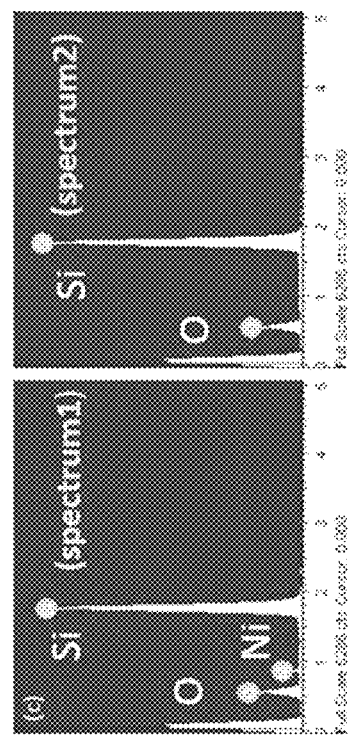
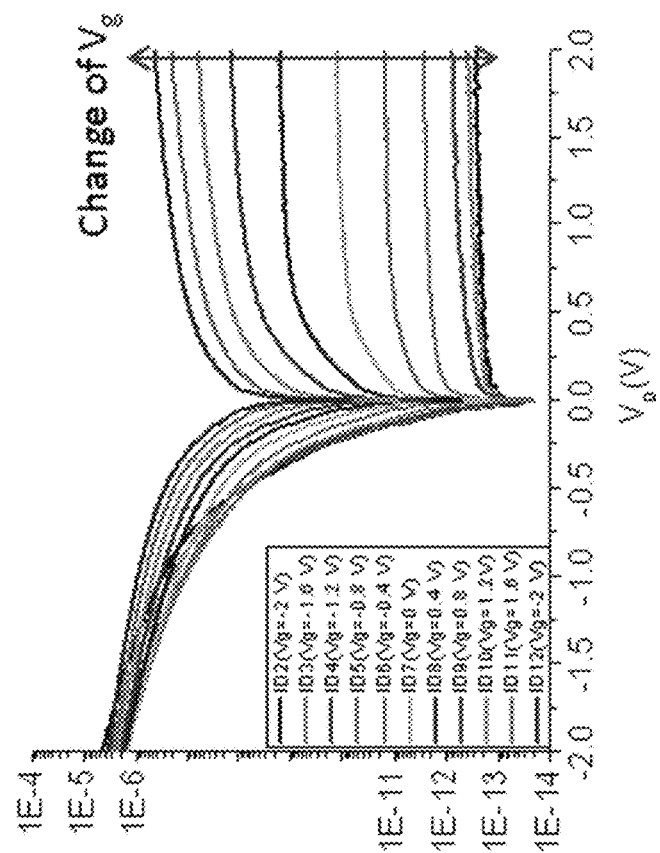
FIG. 13D
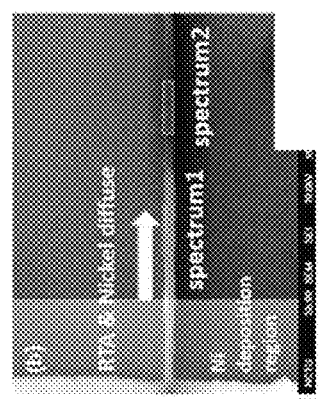
FIG. 13B
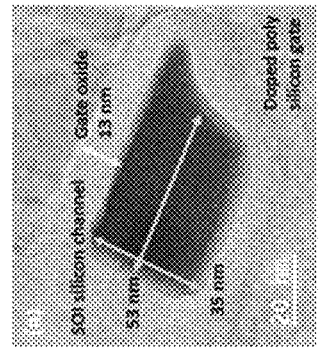
FIG. 13A
FIG. 13C

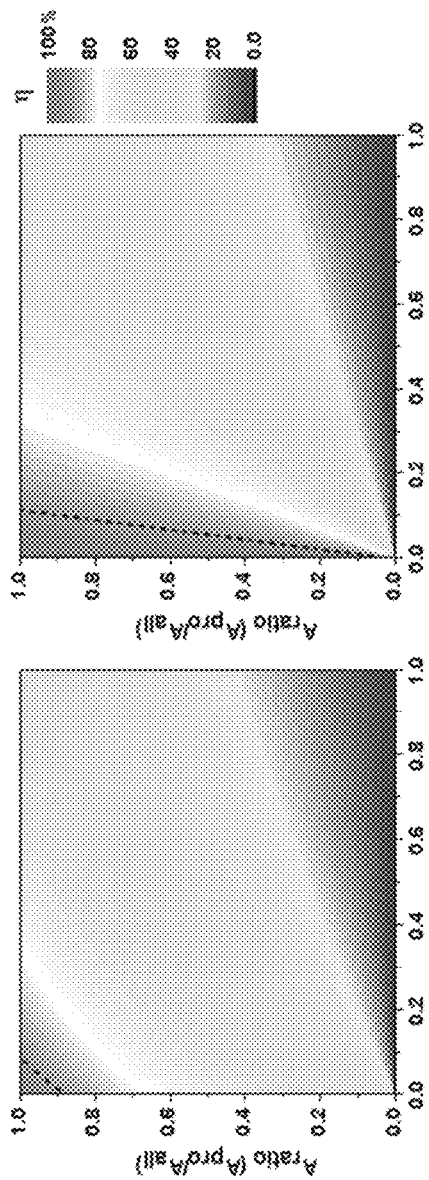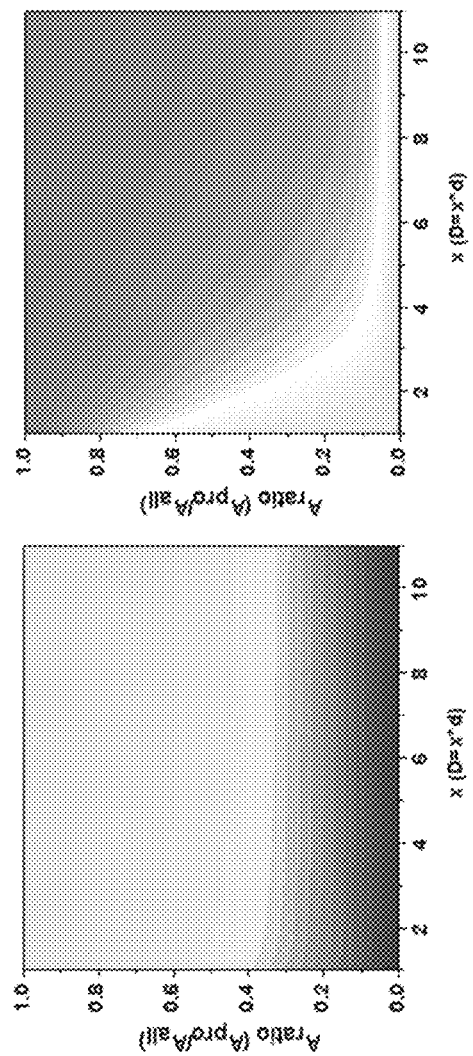
FIG. 18A  FIG. 18B  FIG. 18C  FIG. 18D

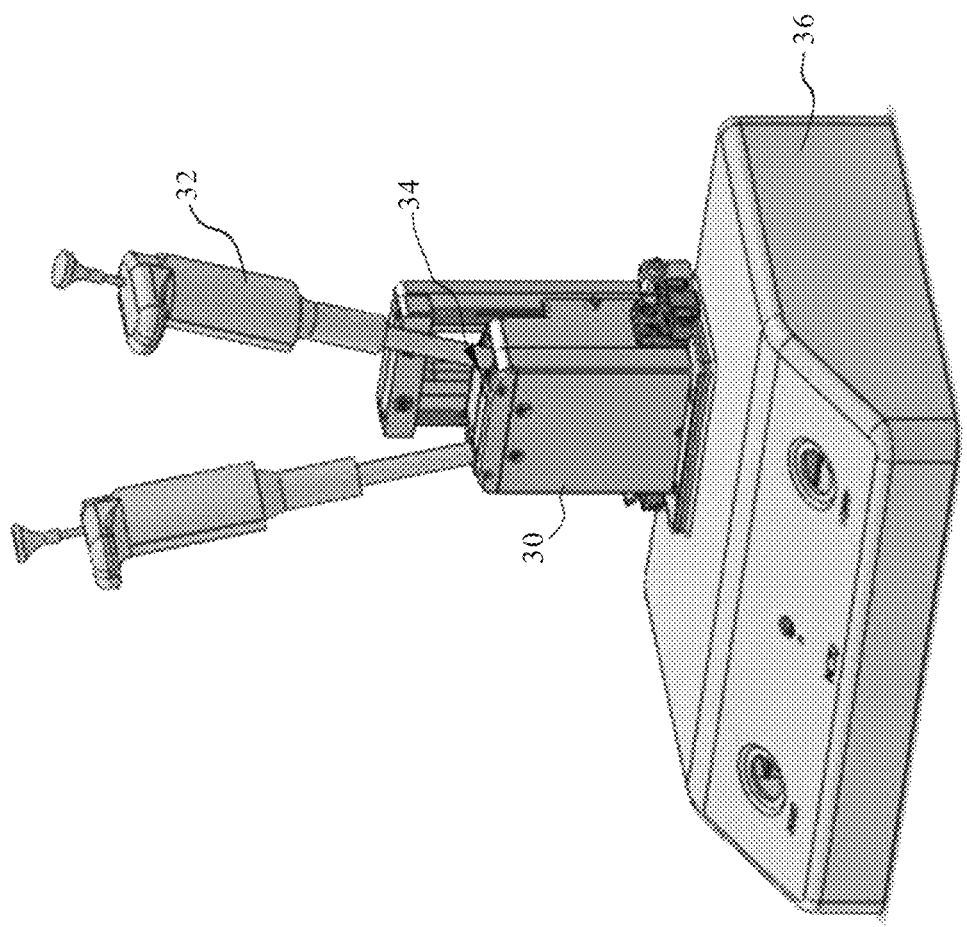

BIOLOGICAL SENSING SYSTEM

CROSS-REFERENCE RELATED APPLICATION

The present disclosure claims the benefit of U.S. Provisional Application No. 62/409,931, filed on Oct. 19, 2016, which is hereby incorporated by reference as if fully set forth herein.

BACKGROUND OF THE INVENTION

1. Field of the Invention

The present disclosure relates to a biological sensing system using extended gate and gate-all-around (GAA) silicon nanowire devices.

2. The Prior Arts

The Field effect transistor (FET) is a semiconductor device provided for controlling the magnitude of a current by an electric field effect. Since the FET has the advantages of a small volume, a light weight, a power-saving feature, a long life, a high gate input impedance, a low noise, a good thermal stability, a strong radiation resistance and a well-established manufacturing procedure, the scope of applicability of the field-effect transistor is very broad, particularly in the fields of large scale integrated circuit (LSI) and very large scale integrated circuit (VLSI). Since a nano-dimension field effect transistor has a very high electric potential sensitivity, it can be used as a basic structure of a bio-sensor and applied in a bio-sensing area. However, a FET channel made of carbon nanotubes has difficulties of positioning carbon nanotubes, separating carbon nanotubes with both metal and semiconductor properties, decorating a surface of the carbon nanotube, and manufacturing large-area FET channels. On the other hand, the silicon nanowire field effect transistor adopting a top-down process technology incurs expensive manufacturing process and cost so that the cost of per detection is too high to deploy in biosensing applications. If a bottom-up process technology is adopted, then there will be difficulties of positioning silicon nanowires, controlling a uniform radius of the silicon nanowires, and maintaining a good yield rate for a large-area manufacturing process. Moreover, it is very difficult to control the uniformity of surface modifications for specific binding on the surface of nanowire devices (nanowire FETs, nanowire diodes etc.) so that quantitative biosensing using nanowire FETs becomes unrealistic.

Moreover, as shown in FIG. 1A, the traditional biosensing using a sensing chip 10 and a MOSFET 12 has been demonstrated in many studies. FIG. 1B is a cross-sectional diagram of a traditional MOSFET. However, since the electrical coupling between the sensing chips and the MOSFET is not optimized; the sensitivity is too low to compete with ELISA or other modern sensing techniques like SPR and QCM.

In view of these shortcomings of the prior art, how to effectively design and optimize a sensing element integrating extended gates with gate-all-around (GAA) silicon nanowire devices has become one of the important issues.

SUMMARY OF THE INVENTION

In light of the foregoing drawbacks of the prior art, an objective of the present disclosure is to provide a biological sensing system. According to a first exemplary of the present disclosure, The biological sensing system includes a junctionless nanowire field-effect transistor, having a source terminal, a drain terminal and a gate terminal, wherein the gate terminal is electrically connected to and surrounds the gate of a junctionless silicon nanowire or the gate terminal is electrically connected to a gate of a junctionless silicon nanobelt, the diameter of the junctionless silicon nanowire is less than 20 nm and the channel thickness of the junctionless silicon nanobelt is less than 15 nm; and a sensing chip, having at least one extended gate, wherein that at least one extended gate is a sensing electrode, and the sensing electrode of the sensing chip is coupled to the gate terminal of the junctionless nanowire field-effect transistor, wherein an area ratio of an electrode area of the sensing electrode to a total sensing chip area, a thickness ratio of an oxide thickness of the sensing electrode to a bulk oxide dielectric film thickness of the sensing chip and a capacitance ratio of a gate capacitor of the junctionless silicon nanowire or a gate capacitor of the junctionless silicon nanobelt to an electrode capacitor of the sensing electrode are optimized by means of an equivalent circuit so as to obtain optimized potential coupling efficiency between the sensing electrode and the gate terminal.

In accordance with a second exemplary embodiment of the present disclosure, the present disclosure also provides a biological sensing system. The biological sensing system includes an inversion mode nanowire field-effect transistor, having a source terminal, a drain terminal and a gate terminal, wherein the gate terminal is electrically connected to and surrounds a gate of an inversion mode silicon nanowire or the gate terminal is electrically connected to a gate of an inversion mode silicon nanobelt, the diameter of the inversion mode silicon nanowire is less than 20 nm and the channel thickness of the inversion mode silicon nanobelt is less than 15 nm; and a sensing chip, having at least one extended gate, wherein the at least one extended gate is a sensing electrode, and the sensing electrode of the sensing chip is coupled to the gate terminal of the inversion mode nanowire field-effect transistor, wherein an area ratio between an electrode area of the sensing electrode and a total sensing chip area, a thickness ratio of an oxide thickness of the sensing electrode to a bulk oxide dielectric film thickness of the sensing chip and a capacitance ratio of a gate capacitor of the inversion mode silicon nanowire or a gate capacitor of the inversion mode silicon nanobelt to an electrode capacitor of the sensing electrode are optimized by means of an equivalent circuit so that potential coupling efficiency between sensing electrode and gate is optimized.

In accordance with a third exemplary embodiment of the present disclosure, the present disclosure also provides a biological sensing system. The biological sensing system includes a gated nanowire diode, having a source terminal, a drain terminal and a gate terminal, wherein the gate terminal is electrically connected to and surrounds a gate of a gated silicon nanowire diode or the gate terminal is electrically connected to a gate of a gated silicon nanobelt diode, the diameter of the gated silicon nanowire is less than 20 nm and the channel thickness of the gated silicon nanobelt diode is less than 15 nm; and a sensing chip, having at least one extended gate, wherein the at least one extended gate is a sensing electrode, and the sensing electrode of the sensing chip is coupled to the gate terminal of the gated nanowire diode transistor, wherein an area ratio between an electrode area of the sensing electrode and a total sensing chip area, a thickness ratio of an oxide thickness of the sensing electrode to a bulk oxide dielectric film thickness of the sensing chip and a capacitance ratio of a gate capacitor of the gated silicon nanowire diode or a gate capacitor of the gated silicon nanobelt diode to an electrode capacitor of the sensing electrode are optimized by means of an equivalent circuit so that potential coupling efficiency between sensing electrode and gate is optimized.

In accordance with the exemplary embodiments, the present disclosure may further includes a preamplifier module and a postamplifier module, wherein the sensing chip is disposable and contacts with the preamplifier module via a plurality of pogo pins, the preamplifier module is electrically connected to the postamplifier module, and the postamplifier comprises a digital-to-analog converter (DAC), a analog-to-digital converter (ADC), a micro controller, an operational amplifier (opamp), a reference electrode bias terminal, a USB terminal and a power supply terminal.

In accordance with the exemplary embodiments, the present disclosure may further includes a mechanical structures, having a slider, a guide pipette, a pipette slide cover and a metal chassis, wherein the slider is used for alignment and contacts between the sensing chip and a plurality of pogo pins; the guide pipette is to fastened the pipette tip at the same level atop the sensing electrode; the pipette slide cover is used to avoid light interference; and the metal chassis is used to avoid electromagnetic interference.

BRIEF DESCRIPTION OF THE DRAWINGS

The present disclosure will be apparent to those skilled in the art by reading the following detailed description of a preferred embodiment thereof, with reference to the attached drawings, in which:

FIGS. 4A-4F show a cross-sectional view of a spacer nanowire fabrication process according to the present disclosure.

FIGS. 6G-6L show a cross-sectional view of an inversion mode (IM) nanowire FET according to a first preferred embodiment of the present disclosure.

FIGS. 8G-8K show a cross-sectional view of a junctionless (JL) nanowire FET according to a second preferred embodiment of the present disclosure.

FIGS. 10G-10M show a cross-sectional view of a nanowire diode with a gate according to a third preferred embodiment of the present disclosure.

FIGS. 13A-13D show a cross-sectional TEM image of silicon nanowire GAA structure, a SEM image of NiSi/Si nanowire diode, a spectrum showing material compositions at NiSi and Si regions by EDS and I-V characteristics of NiSi—Si nano wire diode at different gate voltages, respectively.

FIG. 18A shows potential coupling efficiency η with respect to $A_{ratio}$ and x when Q atop of a sensing electrode; $A_{ratio}$ and $C_{ratio}$ vary when x=1.

FIG. 18B shows potential coupling efficiency η with respect to $A_{ratio}$ and x when Q atop of a sensing electrode; $A_{ratio}$ and $C_{ratio}$ vary when x=1000.

FIG. 18C shows potential coupling efficiency η with respect to $A_{ratio}$ and x when Q atop of a sensing electrode; $A_{ratio}$ and x vary when $C_{ratio}$=1.

FIG. 18D shows potential coupling efficiency η with respect to $A_{ratio}$ and x when Q atop of a sensing electrode; $A_{ratio}$ and x vary when $C_{ratio}$=0.01.

FIG. 22 shows a mechanical sensing system according to the present disclosure.

DETAILED DESCRIPTION OF THE PREFERRED EMBODIMENT

The accompanying drawings are included to provide a further understanding of the disclosure, and are incorporated in and constitute a part of this specification. The drawings illustrate preferred exemplary embodiments of the disclosure and, together with the description, serve to explain the principles of the disclosure.

The following preferred exemplary embodiments of the present disclosure describe a biological sensing system.

Figures 1A, 1B:
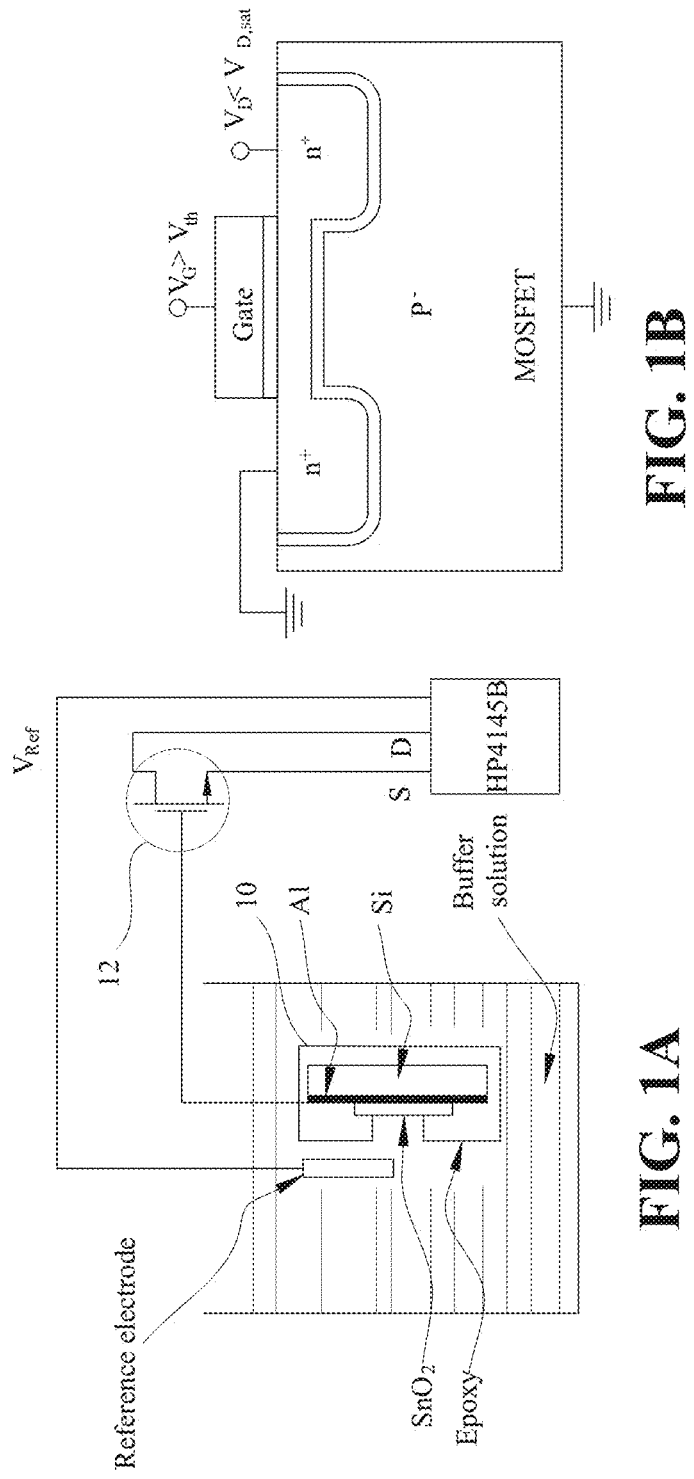
FIG. 1A is a diagram of a traditional extended gate sensing structure using a traditional MOSFET.
FIG. 1B is a cross-sectional diagram of a traditional MOSFET.
Figure 2:
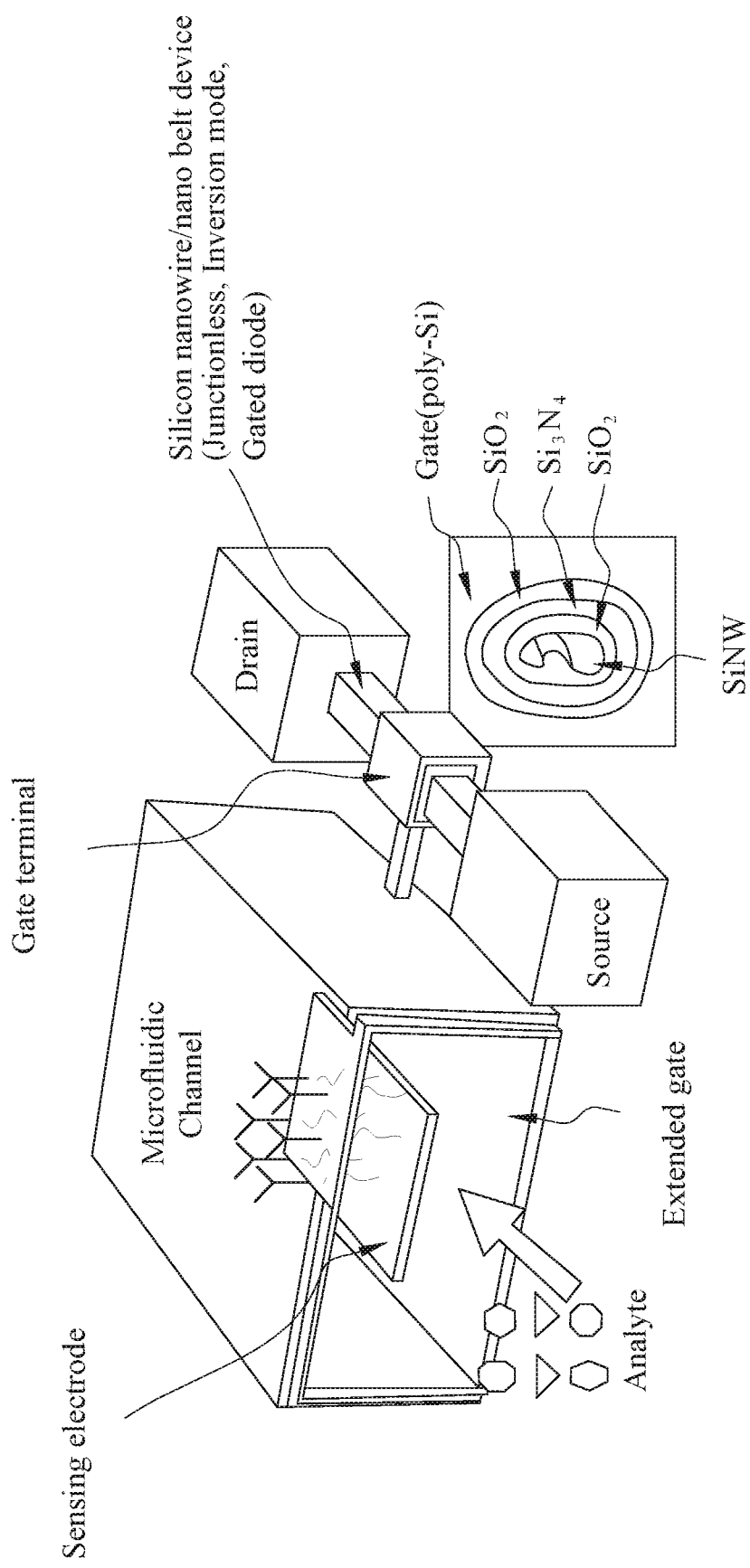
FIG. 2 shows a schematic diagram of an extended gate gate-all-around (GAA) silicon nanowire device biosensing platform with a microfluidic channel.

FIG. 2 shows a schematic diagram of an extended gate gate-all-around (GAA) silicon nanowire device biosensing platform with a microfluidic channel. As shown in FIG. 2, the lower right inset is a SEM image showing a channel of a nanowire device surrounded by gate dielectrics and the gate. The extended gate (sensing elecode) on a sensing chip is disposable and the expensive GAA nanodevice is located inside a sensing system.

According to the present disclosure, three different GAA silicon nanowire (SiNW) devices (Inversion mode (IM) nanowire Field-effect transistor, Junctionless (JL) nanowire Field-effect transistor and nanowire diode with gate) are provided; these SiNW devices can be used as transducers to amplify the induced potential voltage resulted from specific binding at the surface of sensing electrode.

Preparation of SiNWs

The body of three different nanowire devices is the Si NW. The correspondent 2D and 3D process flows of SiNW preparation using the modified sidewall spacer technique via conventional optical lithography are provided as follows.

Control of the Dimensions of the SiNW

Figure 3A:
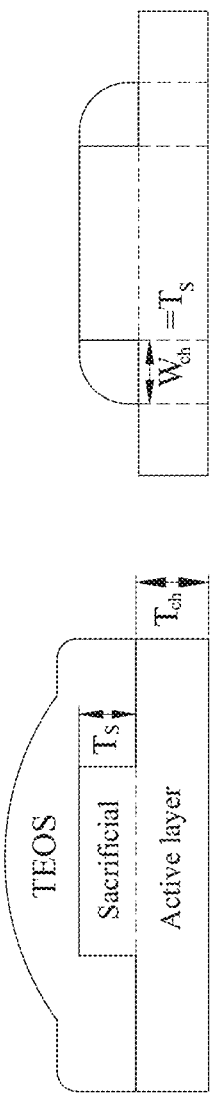
FIGS. 3A-3B show a cross-sectional view of controlling the dimensions of a spacer nanowire according to the present disclosure.
Figure 3B:
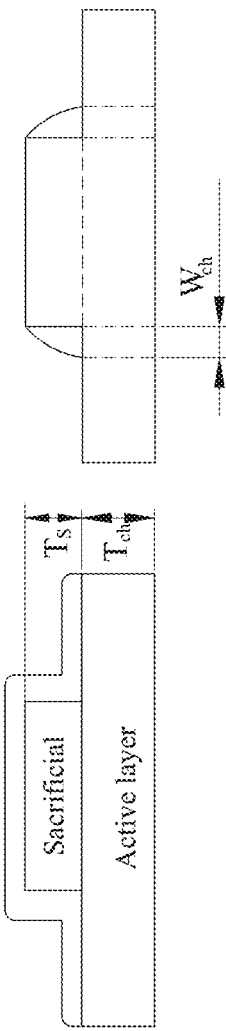
Figure 5A:
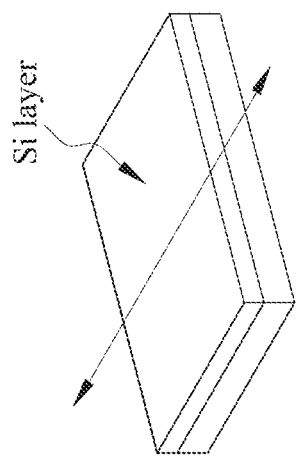
FIGS. 5A-5F show a three-dimensional view of the spacer nanowire fabrication process according to the present disclosure.
Figure 5B:
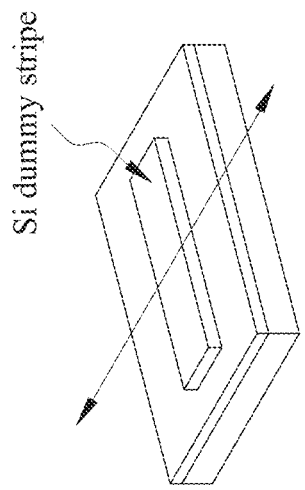
Figure 5C:
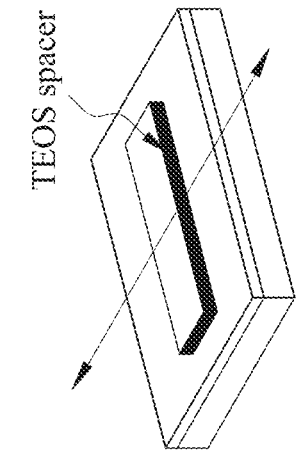
Figure 5D:
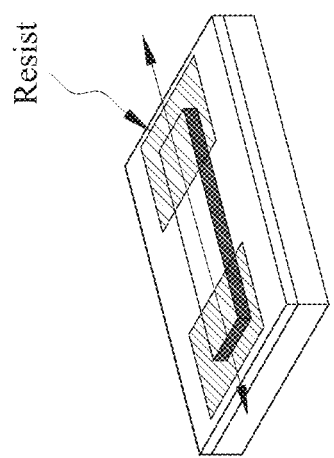
Figure 5E:
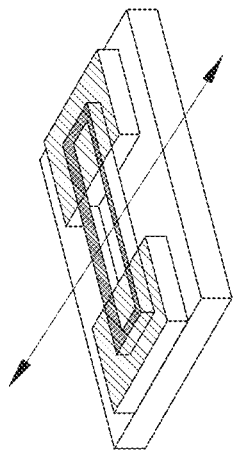
Figure 5F:
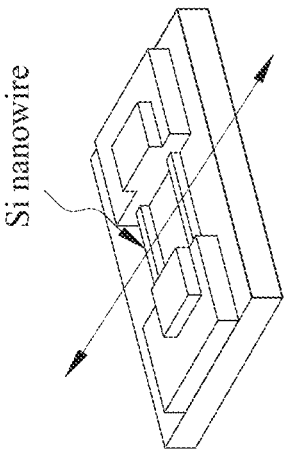
Figure 7G:
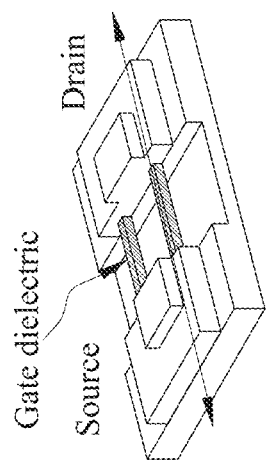
FIGS. 7G-7L show a three-dimensional view of the IM nanowire FET according to the first preferred embodiment of the present disclosure.
Figure 7H:
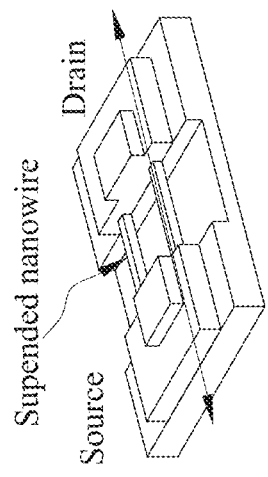
Figure 7I:
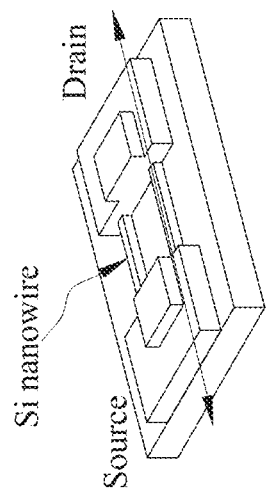
Figure 7J:
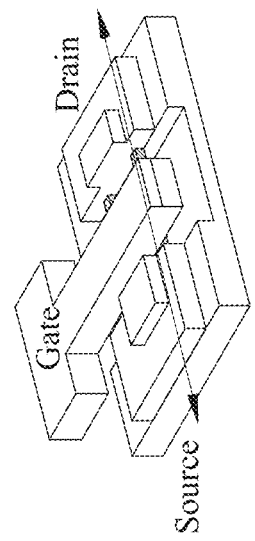
Figure 7K:
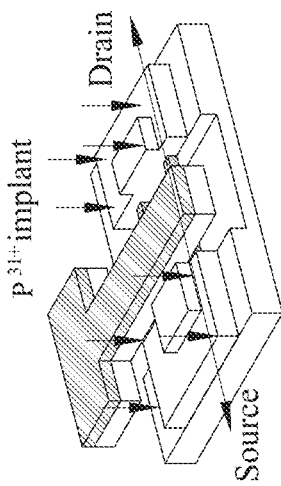
Figure 7L:
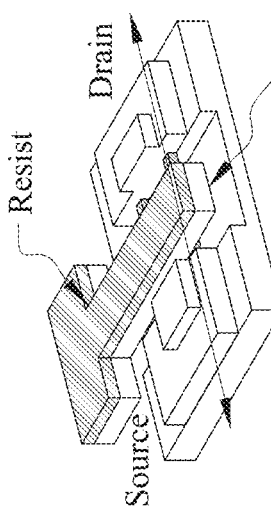
Figure 9G:
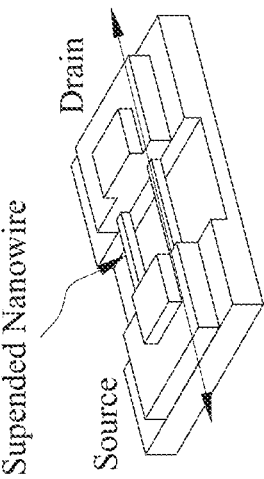
FIGS. 9G-9K show a three-dimensional view of the JL FET according to the second preferred embodiment of the present disclosure.
Figure 9H:
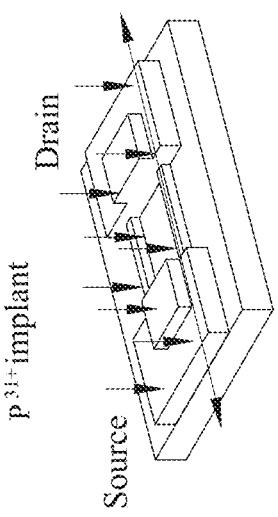
Figure 9I:
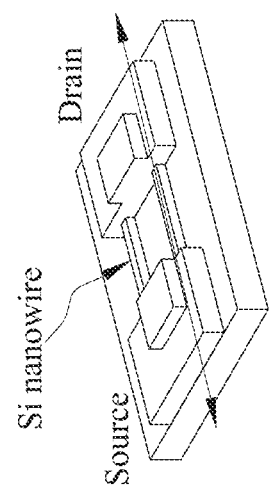
Figure 9J:
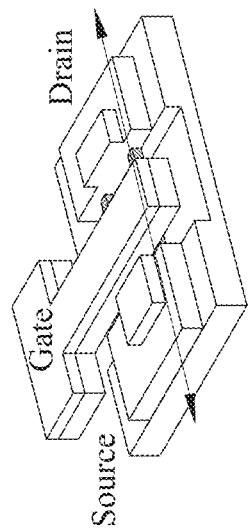
Figure 9K:
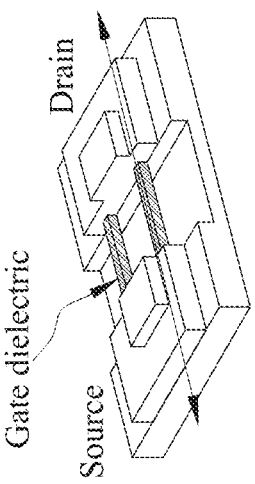
Figure 11G:
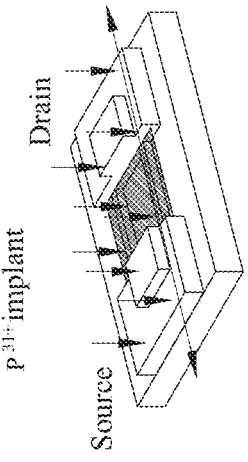
FIGS. 11G-11M show a three-dimensional view of the nanowire diode with the gate according to the third preferred embodiment of the present disclosure.
Figure 11J:
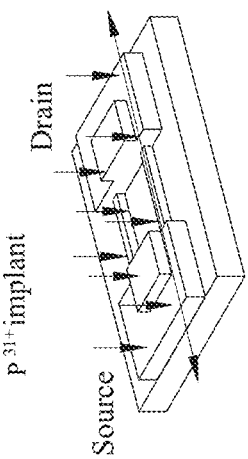
Figure 11M:
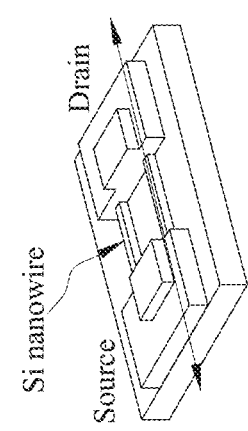
Figure 11H:
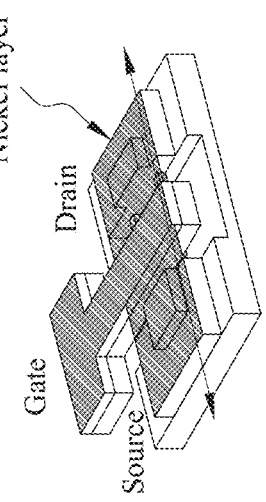
Figure 11K:
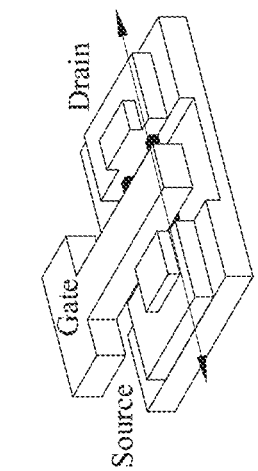
Figure 11L:
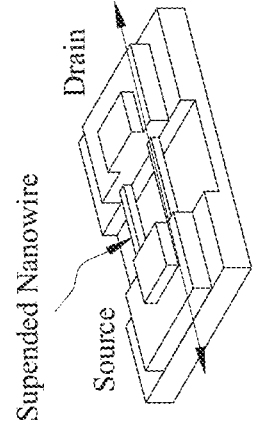
Figure 11I:
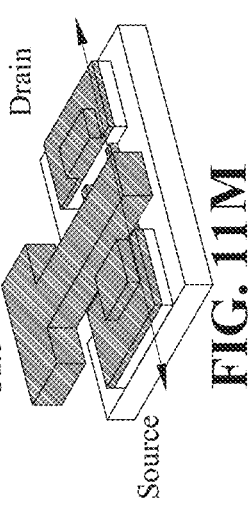

The control of SiNW dimension is very important to obtain a high transconductance device, this is, having a SiNW device with a very small subthreshold swing (SS). An ideal device possesses a SS~60 mV/dec. Two ways to control the dimension of a SiNW are shown in FIGS. 3A-3B. In comparison, deposition of a thick TEOS is easier than depositing a thin TEOS with good conformity; therefore, the process is adopted, as shown in FIG. 3A. The SiNW with width <15 nm and height <45 nm can be obtained using the process, as shown in FIG. 3B. Also, a device with dimensions smaller than the above mentioned presents SS near 63 mV/dec.

Spacer NW Fabrication

The devices fabrication start from the SOI wafer with 70 nm active layer (top-Si) and 200 nm oxide layer [FIG. 4A]. Next, the top-Si layer was patterned into a mesa structure through optical lithography, which was followed by reactive ion etching (RIE). The top-Si layer was transformed into two parts; the thicker part served as a dummy strip, and the thinner one served as device active layer. [FIG. 4B]. Then, a 60-nm thick tetraethylorthosilicate (TEOS) layer was deposited using LPCVD, and then etched through RIE, leaving TEOS spacers [FIG. 4C]. Before NW formation, the source and drain (S/D) regions were defined through an I-line stepper [FIG. 4D]. Next, the top-Si layer was etched through high-selective RIE, and the NWs were formed through TEOS hard masks [FIG. 4E]. After NWs formation, the TEOS hard masks were removed in 1:50 diluted HF solution[FIG. 4F]. The cross-sectional views are shown in FIGS. 5A-5F along the lines correspondently.

Inversion Mode (IM) Nanowire Field-Effect Transistor

The NWs is prepared by the sidewall spacer process [FIG. 6G]. Then the NWs are suspended during RCA cleaning [FIG. 6H]. After that, the gate oxide layer is grown by LPCVD [FIG. 6I], and the in-situ doped poly-Si layer is deposited and patterned as a poly-Si gate [FIG. 6J]. Then the self-align phosphorus implantation is performed at a dose of 5E15 cm$^{-2}$ [FIG. 6K]. Finally, the dopant is activated and the Al metallization is performed [FIG. 6L]. The cross-sectional views are shown in FIGS. 7A-7L along the lines correspondently.

Junctionless (JL) Nanowire Field-Effect Transistor

The NWs are prepared by the sidewall spacer process [FIG. 8G]. Then the phosphorus implantation is performed at a dose of 1E19 cm$^{-3}$~5 E19 cm$^{-3}$ [FIG. 8H]. The NWs are suspended during RCA cleaning [FIG. 8I]. After the dopant is activated, the gate oxide layer is grown by LPCVD [FIG. 8J]. Then the in-situ doped poly-Si layer is deposited and patterned as a poly-Si gate [FIG. 8K]. Finally, the Al metallization is performed. The cross-sectional views are shown in FIGS. 9G-9K along the lines correspondently.

Nanowire Diode with Gate (Also Called Gated Nanowire Diode)

The NWs are prepared by the sidewall spacer process [FIG. 10G]. Then the phosphorus implantation was performed at a dose of 1E18 cm$^{-3}$ [FIG. 10H]. For a lower contact resistor, the second implantation ss performed at the S/D region [FIG. 10I]. Then the NWs are suspended during RCA cleaning [FIG. 10J]. After the dopant is activated, the gate oxide layer is grown and the poly-Si gate is patterned by RIE [FIG. 10K]. Subsequently the Nickel layer (Ti, Co are also candidate matals and IC process compatible) is deposited [FIG. 10L]. Then the device is annealed at 500° C. for 30 s to form a silicide contact, and the silicide will diffuse into the NW channel to form a Schottky contact under the gate [FIG. 10M]. The cross-sectional views are shown in FIGS. 11G-11M along the lines correspondently.

Sensing Mechanisms of the GAA SiNW Devices

With regard to the IM and JL GAA devices, the current vs. induced potential follows the equation (1):

$$I \approx e^{(-\frac{qVg}{kT})}e^{-\frac{q\Delta\varphi}{kT}} \quad (1)$$

For the SiNW diode with gate, the current vs. induced potential follows the equation (2):

$$I \approx A*T^2 e^{(-\frac{q\varphi Bn}{kT})}e^{-\frac{q\Delta\varphi}{kT}} \quad (2)$$

where

Δφ: induced gate potential change resulted from specific binding;

Vg: gate bias;

$\varphi_{Bn}$: metal silicide/silicon barrier height;

k: Boltzmman constant; and

T: temperature.

Devices Fabrication and Electrical Characteristics

Figures 12A, 12B:
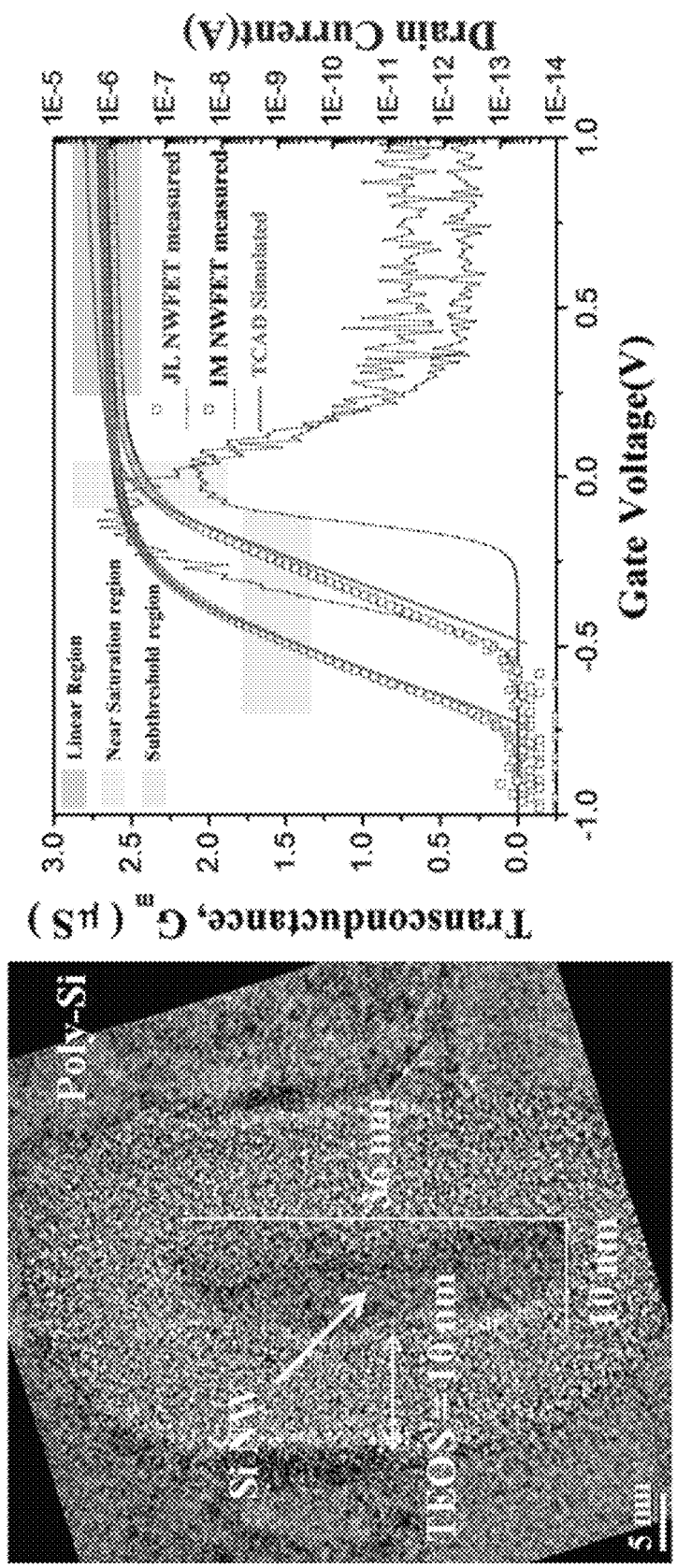
FIGS. 12A-12B show a cross-sectional TEM image of silicon nanowire GAA structure and a transfer characteristics and transconductance of IM and JL GAA nanowire FETs, respectively.

FIGS. 12A-12B show a cross-sectional TEM image of silicon nanowire GAA structure and a 10-nm TEOS oxide dielectric as well as a transfer characteristics and transconductance of IM and JL GAA nanowire FETs, respectively. As shown in FIG. 12A, the dimension of SiNW channel is ~11 nm wide and ~36 nm high. IM and JL devices present ~63 mV/dec close to the ideal substhreshold swing. It should be noted that the JL nanowire device exhibits a better transconductance (e.g. 2.7 μS).

FIGS. 13A-13D show a cross-sectional TEM image of silicon nanowire GAA structure, a SEM image of NiSi/Si nanowire diode, a spectrum showing material compositions at NiSi and Si regions by EDS and I-V characteristics of NiSi—Si nano wire diode at different gate voltages, respectively. As shown in FIG. 13A, the TEOS oxide dielectric is about 13 nm and a poly-Si gate with channel width ~35 nm and a thickness ~53 nm. The SEM image of NiSi/Si nanowire diode is shown in FIG. 13B. The spectrum demonstrates the material compositions at NiSi and Si regions by EDS, as shown in FIG. 13C. FIG. 13D shows the I-V characteristics of the NiSi—Si NW diode at different gate voltages. Near seven order of current change can be observed at $V_D$=2V when Vg changed from −2V to 2 V.

Sensing Chip (Extended Gate)

Figure 14:
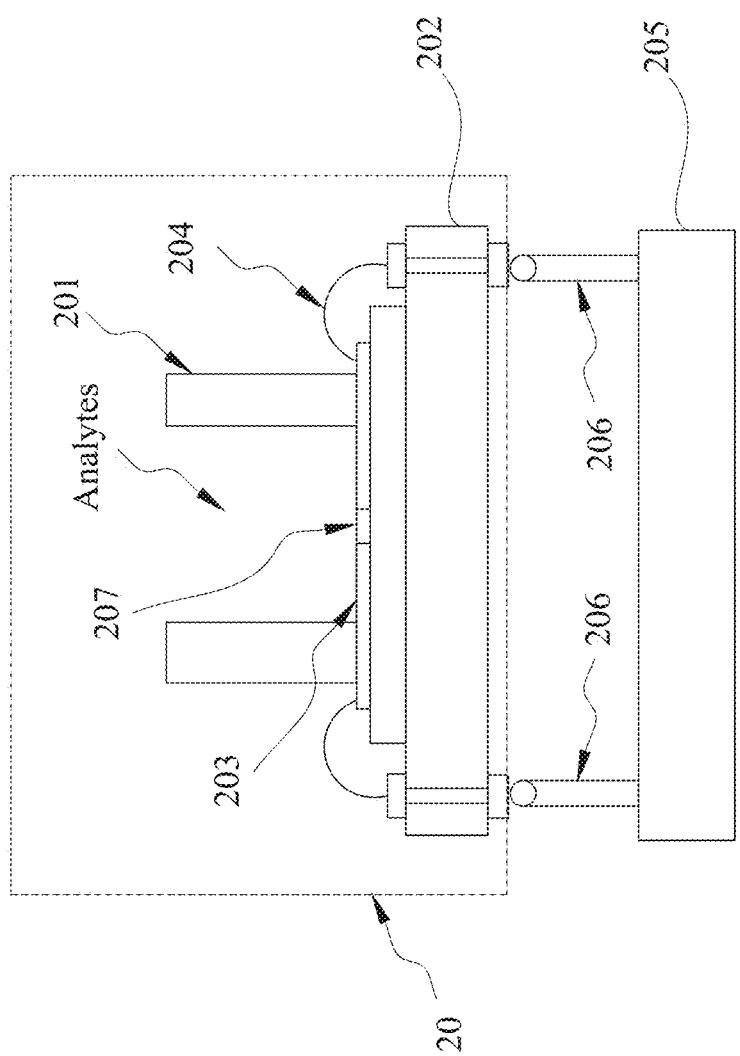
FIG. 14 shows a cross-sectional view of a sensing chip that is arranged on a PCB via Pogo pins according to the present disclosure.

FIG. 14 shows a cross-sectional view of a sensing chip 20 that is arranged on a PCB 202 via Pogo pins 206 according to the present disclosure. The sensing chip 20 includes a silicon chip (not shown) with sensing electrodes 203, a fluid well 201 and a PCB 202. The fluid well 201 is disposed on the sensing electrodes 203, and the sensing electrodes 203 is electrically connected to the PCB 202 by a bondwire 204.

Figure 15:
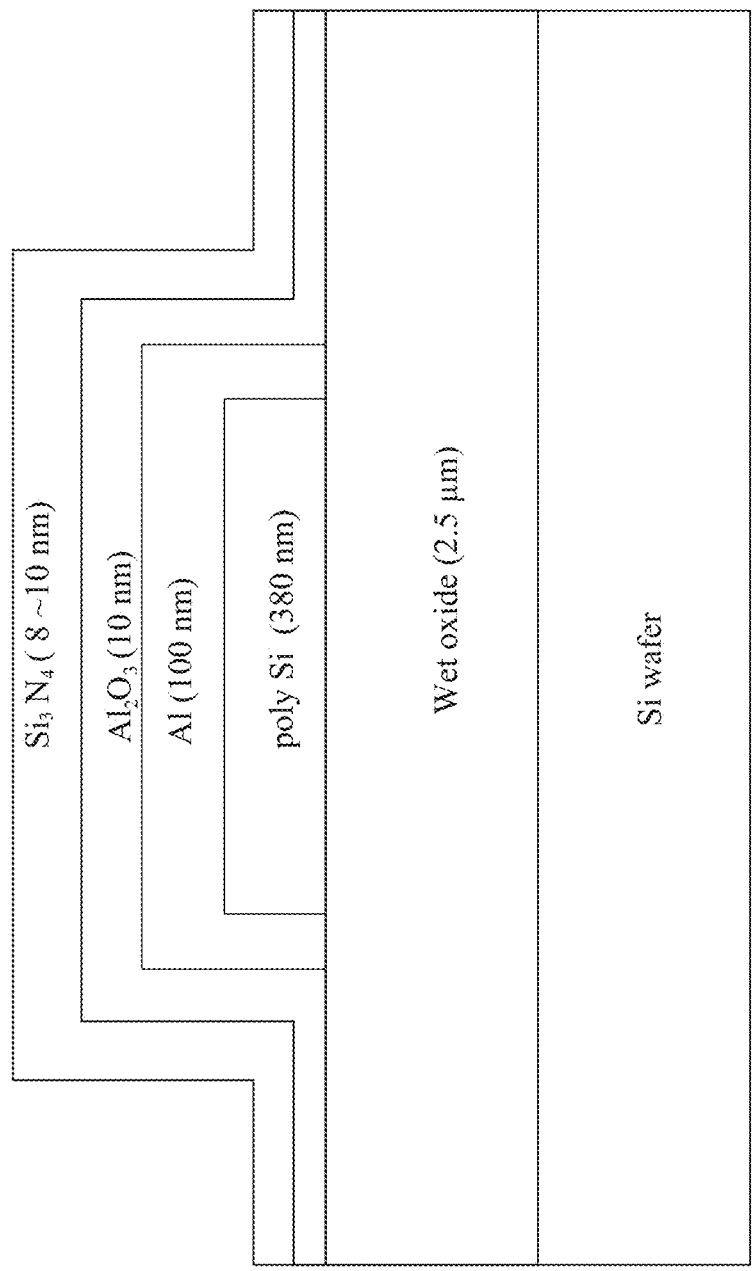
FIG. 15 shows a cross-sectional view of a sensing electrode on sensing chip according to the present disclosure.

The sensing electrodes are prepared with a silicon wafer as a substrate. Then, a 2.5-μm (at least 2 μm to reduce charge interference outside the sensing electrodes) thick $SiO_2$ was grown by thermal oxidation. A 380-nm heavily doped poly-Si is grown by means of LPCVD. Then, the diameter of the sensing electrodes is defined by optical lithography. Samples are coated with a 100-nm thick Aluminum film and followed by a 10-nm high-k $Al_2O_3$ layer (5~10 nm is fine to maintain a high capacitive property) deposition via atomic layer deposition (ALD). High-k materials (like $HfO_2$, $Ta_2O_5$ etc.) are all also applicable. Subsequently, an 8-nm $Si_3N_4$ thin film (at least 5 nm to prevent metal ions ($Na^+$, $K^+$ . . . ) penetration from PBS buffer) is coated via PECVD atop the $Al_2O_3$ layer to prevent metal ion from the analyte during measurement. The equivalent oxide thickness (EOT) of 10-nm $Al_2O_3$ layer and 8-nm $Si_3N_4$ are about 9.5 nm. The cross-sectional view of a sensing electrode is depicted in FIG. 15.

Figure 16:
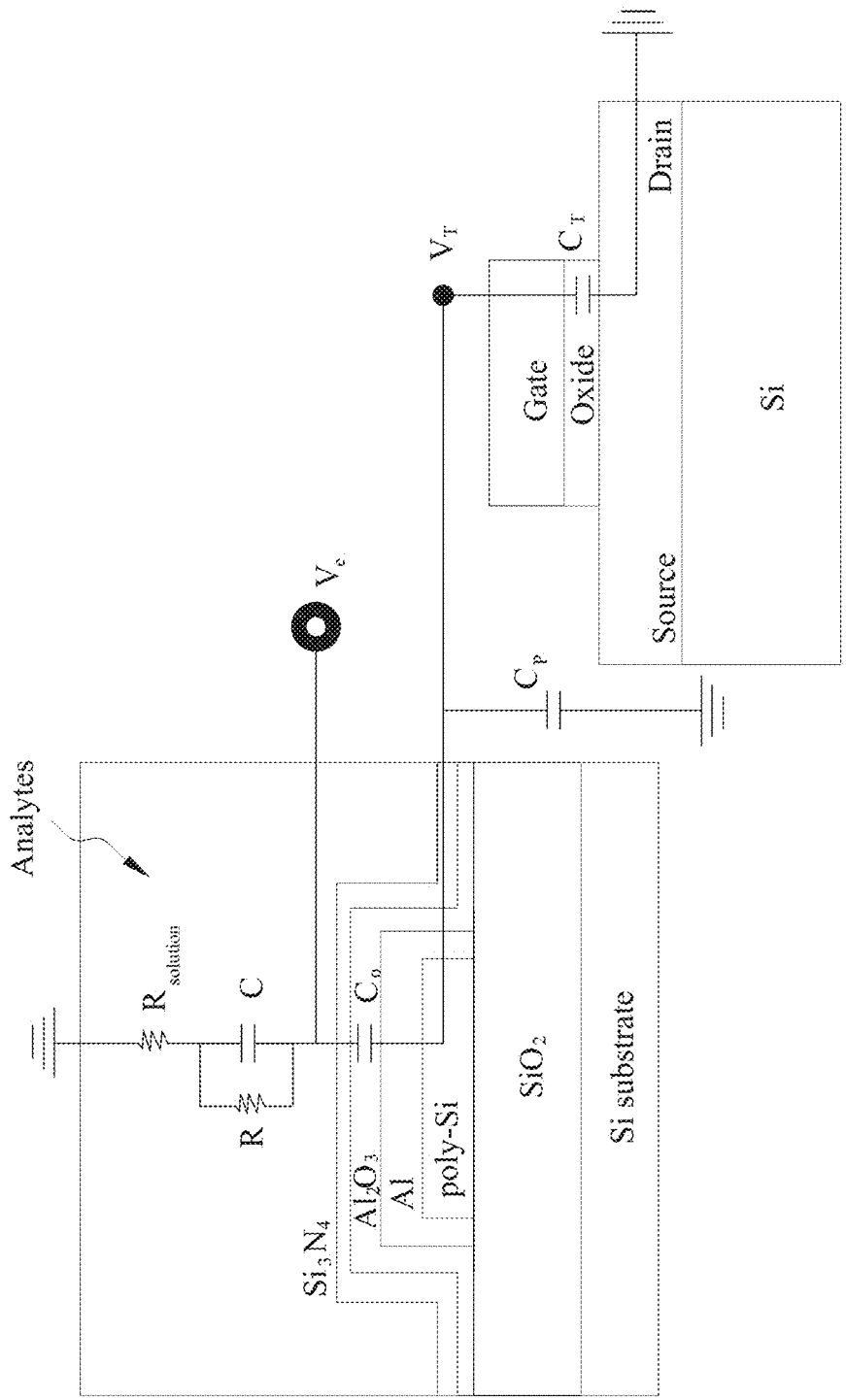
FIG. 16 shows an equivalent circuit of a sensing electrode and a nanowire device according to the present disclosure.

Capacitor Matching Between Sensing Electrode and the Gate Capacitor of SiNW Devices FIG. 16 shows an equivalent circuit of a sensing electrode and a GAA nanowire device according to the present disclosure. Moreover, FIGS. 17A-17D show four types of equivalent circuits of EG silicon nanodevice sensing system.

Figure 17A:
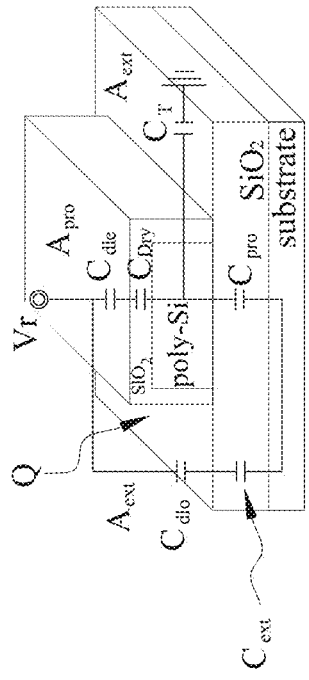
FIGS. 17A-17D show four types of equivalent circuits of EG silicon nanodevice sensing system.
Figure 17C:
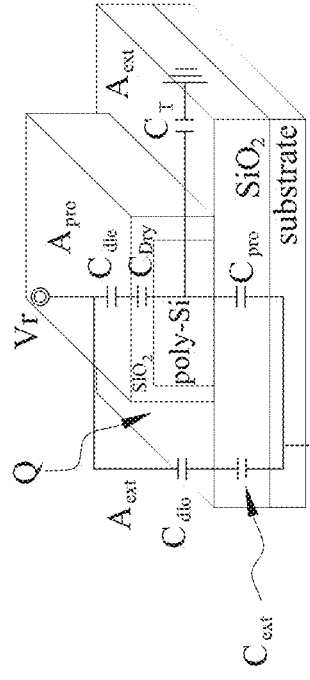
Figure 17B:
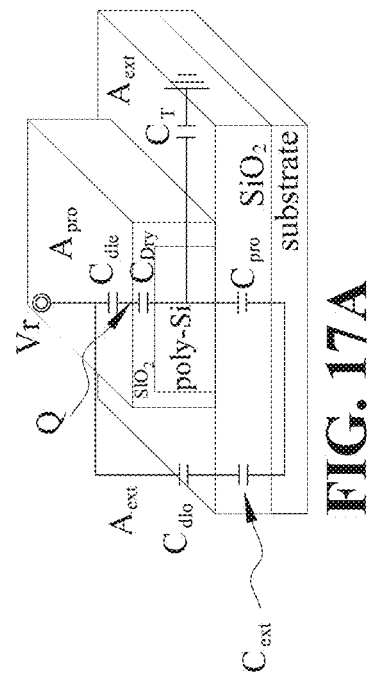

The charge density Q is bound on a sensing electrode [FIG. 17A. type A] and bound on the area outside the sensing electrode [FIG. 17B, type B], when the substrate of the sensing electrode is floating. The charge density Q is bound on the sensing electrode [FIG. 17C, type C] and bound on the area outside the sensing electrode [FIG. 17D, type D], when the substrate of the sensing electrode is grounded. Table 1 shows the symbols and default values of simulation parameters.

Charges induced from specific binding biomolecules are redistributed between the two parallel capacitors ($C_{dle}$ and $C_{Dry}$). According to the equivalent circuit, the gate potential voltage of the SiNW device induced by a specific binding, $V_T$, can be described by the equation (3)-(5), $$V_T = \frac{C_{Dry}}{C_1 + C_{Dry}} \times V_{e,typeA} \quad (3)$$

where $$V_{e,typeA} = \frac{Q}{\frac{C_1 \times C_{Dry}}{C_1 + C_{Dry}} + C_{dle}} \quad (4)$$

$$C_1 = \frac{C_{ext} \times C_{pro} \times C_{dlo}}{(C_{ext} \times C_{pro}) + (C_{pro} \times C_{dlo}) + (C_{ext} \times C_{dlo})} + C_T \quad (5)$$

TABLE 1

Symbols and default values of simulation parameters.

| Parameter | Symbol |
|---|---|
| NWFET capacitor | $C_T$ |
| Electrode capacitor | $C_{Dry}$ |
| Electric double layer capacitor at sensing electrode | $C_{dle}$ |
| Capacitor between sensing electrode and substrate | $C_{pro}$ |

TABLE 1-continued

Symbols and default values of simulation parameters.

| Parameter | Symbol |
|---|---|
| Electric double layer capacitor | $C_{dlo}$ |
| Bulk oxide capacitor outside the sensing electrode | $C_{ext}$ |
| Area outside sensing electrode | $A_{OX1}$ |
| Area of sensing electrode | $A_{OX2}$ |
| Electrode oxide thickness | d |
| Bulk oxide thickness | D |
| SiO2 permittivity | $\varepsilon_{ox} = 3.9\varepsilon_0$ |
| Water permittivity | $\varepsilon_w = 78\varepsilon_0$ |
| Boltzmann constant | $k_B = 1.38 \times 10^{-23}$ J/K |
| Avogadro number | $N_A = 6.022 \times 10^{23}$/mole |
| Elementary charge | $e = 1.602 \times 10^{-19}$ C | where $C_{Dry}$ is capacitance between the stern layer and the sensing electrode; Q is the charge density of specific binding biomolecules; $C_{dle}$ is electric double layer capacitance of area of the sensing electrode; $C_{pro}$ is capacitance between the sensing electrode and the substrate; $C_{dlo}$ and $C_{ext}$ are electric double layer capacitance and bulk oxide capacitance outside the sensing electrode, respectively; and $C_T$ is the gate capacitance of SiNW device. Potential coupling efficiency is defined as $\eta = V_T/V_e \times 100\%$, where $V_e$ is surface potential at the sensing electrode. Two parameters, $A_{ratio} = A_{pro}/A_{all}$, the area ratio of an electrode area of the sensing electrode to a total chip area, and $C_{ratio} = C_T/C_{Dry(max)}$, the capacitance ratio of a gate capacitor of GAA SiNW device to an electrode capacitor of the sensing electrode, are used to optimize the potential coupling efficiency $\eta$. $A_{ratio}$ also depicts the surface coverage of sensing electrode, while $C_{ratio}$ denotes the charge distribution between the sensing electrode and the GAA SiNW device. In equation (3), $C_1 \sim [(C_{ext} \times C_{pro})/(C_{ext} + C_{pro}) + CT]$ is assumed due to $C_{dlo}$ is 50 times larger than $C_{pro}$ and $C_{ext}$ in a high ionic strength environment (PBS>1 mM). The bulk oxide thickness also affects $C_1$ value; therefore a ratio of oxide thickness of the sensing electrode to the bulk oxide dielectric film thickness x (D=x×d) is also defined to optimize the potential coupling efficiency. d is an oxide thickness of the sensing electrode and D is an oxide thickness of the bulk oxide. Table. 1 shows the key parameters that are used in simulation.

FIG. 18A shows potential coupling efficiency $\eta$ with respect to $A_{ratio}$ and x when Q atop of a sensing electrode; $A_{ratio}$ and $C_{ratio}$ vary when x=1. When x=1, since $C_{ratio}$ increases, $\eta$ decreases because of the voltage dividing effect between these two capacitors. There is a linear relationship between $A_{ratio}$ and $V_T$, as a result, Apro is proportional to $C_{Dry}$. A black dash line is indicated for $\eta$ above 90%, as shown in FIG. 18A. The equation of the dash line can be presented as Aratio=1.5×Cratio+0.88, for 0<Cratio≤0.08. On the other hand, as shown in FIG. 18B, $\eta$ more than 90% is increased, when x is increased to 1000. Moreover, the equation of the dash line can be described as Aratio=9.5× Cratio+0.05; 0<Cratio≤0.1, as shown in FIG. 18B. As compared to FIGS. 18A and 18A, when the chip ($A_{all}$) remains the same, the $A_{pro}$ may be less than 17 times when x value increases from 1 to 1000. Therefore, more sensing electrodes can be placed at the same sensing chip by increasing the ratio of oxide thickness to bulk oxide and gate oxide. In addition, FIG. 18C shows potential coupling efficiency $\eta$ with respect to $A_{ratio}$ and x when Q atop of a sensing electrode; $A_{ratio}$ and x vary when $C_{ratio}$=1. x value is not significant to $\eta$, and the maximum $\eta$ may be obtained about 50%. FIG. 18D shows potential coupling efficiency η with respect to $A_{ratio}$ and x when Q atop of a sensing electrode; $A_{ratio}$ and x vary when $C_{ratio}$=0.01. It can be observed that η is increased rapidly when x value increases from 0 to 4 because the $C_{pro}$ value is close to the $C_{Dry}$ value. Thus, since the x value is larger than 10 and both $C_{ext}$ and $C_{pro}$ are decreased, at least an 80% of η can be obtained. Therefore, the potential coupling efficiency >90% resulting from a specific binding on the sensing electrode can effectively be obtained when $C_T \ll C_{Dry}$ and x>10 for type A configuration [FIG. 18A].

The surface outside the electrode of the sensing chip may also capture biomolecules, and the additional signal could interfere the surface potential measured by the GAA SiNW device. Therefore, regarding the type B equivalent circuit (as shown in FIG. 17B), VT is represented by the equation (6)-(9):

$$V_T = \frac{C_3}{C_4} \times V_{e,typeB} \tag{6}$$

where $$V_{e,typeB} = \frac{Q}{C_3 + C_{dlo}} \tag{7}$$

$$C_3 = \frac{C_{ext} \times C_{pro} \times C_4}{(C_{ext} \times C_{pro}) + (C_{pro} \times C_4) + (C_{ext} \times C_4)} \tag{8}$$

$$C_4 = \frac{C_{dle} \times C_{Dry}}{C_{dle} + C_{Dry}} + C_T \tag{9}$$

Figures 19A, 19B:
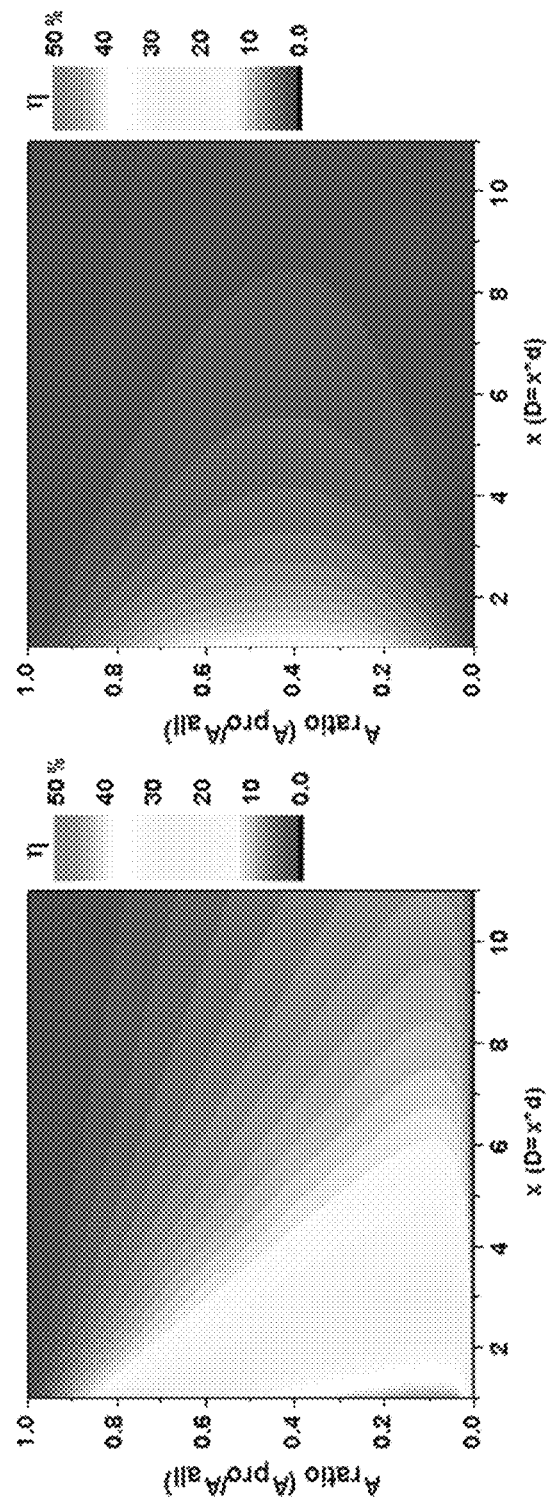
FIGS. 19A-19B show potential coupling efficiency η with respect to $A_{ratio}$ and x when Q locates at area outside the sensing electrode; $A_{ratio}$ and x are variable when $C_{ratio}$=0.01 and $C_{ratio}$=1, respectively.

FIGS. 19A-19B show potential coupling efficiency η with respect to $A_{ratio}$ and x when Q locates at area outside the sensing electrode; $A_{ratio}$ and x are variable when $C_{ratio}$=0.01 and $C_{ratio}$=1, respectively. The maximum potential coupling efficiency η is ~48% for $C_{ratio}$=0.01, while $A_{ratio}$ is around 0.1 and x is around 0.05. However, η is dramatically decreased when $C_{ratio}$=1 since the charge induced potential distributes only to $C_{ext}$ and $C_{pro}$. Moreover, the charges of binding biomolecules does not affect $V_T$, when x value is more than 10. Therefore, x value is the most important design parameter of the sensing electrode in the type B equivalent circuit [FIG. 17B]. According to the simulation results of both type A and type B equivalent circuits, in order to obtain high η and to reduce interference from charge outside the sensing electrode, $C_{ratio}$ should be less than 0.1, the x value may be at least larger than 10.

Figure 17D:
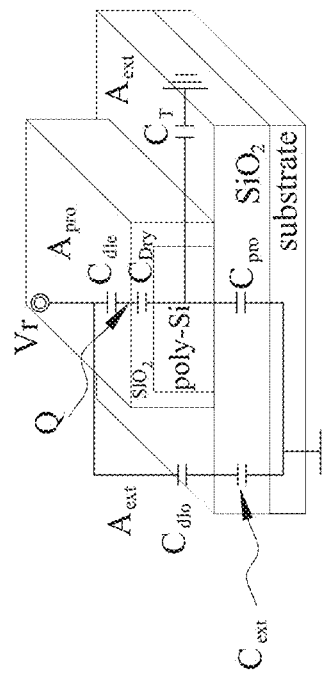

When the substrate of sensing electrode is connected to ground [FIG. 17C; type C], the potential coupling efficiency of the type C equivalent circuit is similar to that of the type A equivalent circuit. However, due to the grounding effect of substrate of the sensing electrode, the impact of x value on η is not as efficient as that of the type A configuration. When the $A_{ratio}$ is the same, $C_1$(type A) value is less than $C_T$ (type C) value, η could approach 100% only on a specific condition, $C_{pro}+C_T \ll C_{Dry}$. Apparently, a higher x value is needed to have the same η for the type C configuration, as compared to the type A configuration. The type D equivalent circuit FIG. 17D is also analyzed. Since all of the capacitors are connected the ground, the charges of binding biomolecules outside the sensing electrode do not induce any potential change for $V_T$.

Influence of Ionic Concentration and Charge Density

Ion concentration in PBS solution has a significant impact on the sensitivity of both SiNW FET sensor and extended gate SiNW sensors. In solution analyte, the charge particles build up a surface potential via electric double layer within the Debye length on the surface of sensing electrode. This electric double layer also forms a capacitor, $C_{dl}$. And this capacitance is ion concentration dependent. Any charge emerged within the Debye length on the surface of sensing electrode can induce a potential change. The relationship between $C_{dl}$, Debye length and ion concentration of buffer solution is represented in the equation (10) and (11).

$$C_{dl} = \varepsilon_0 \varepsilon_r \times \frac{A_{ox}}{\kappa^{-1}} \tag{10}$$

$$\kappa^{-1} = \sqrt{\frac{\varepsilon_0 \varepsilon_r k_B T}{2 N_A e^2 I}} \tag{11}$$

where $\varepsilon_0$ is the permittivity in vacuum, $\varepsilon_r$ is the relative permittivity of the solution, $\kappa-1$ is the Huckel-Debye length of the solution which is strongly dependent to the ion concentration. I is the ionic strength of the electrolyte, and here the unit should be mole/m³, $k_B$ is the Boltzmann constant, T is the absolute temperature in kelvins, $N_A$ is the Avogadro number. e is the elementary charge.

Figure 20A:
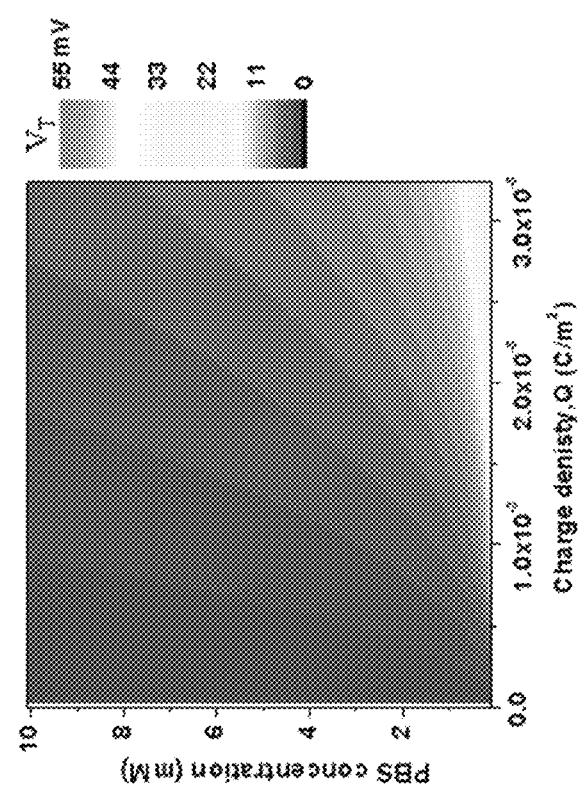
FIGS. 20A-20B show $V_T$ induced by Q (charge density) at various Phosphate-buffered saline (PBS) buffer concentrations for $A_{ratio}$=0.5, $C_{ratio}$=0.01 and x=200 when Q is atop of sensing electrode and when Q is located at a region outside electrode, respectively.
Figure 20B:
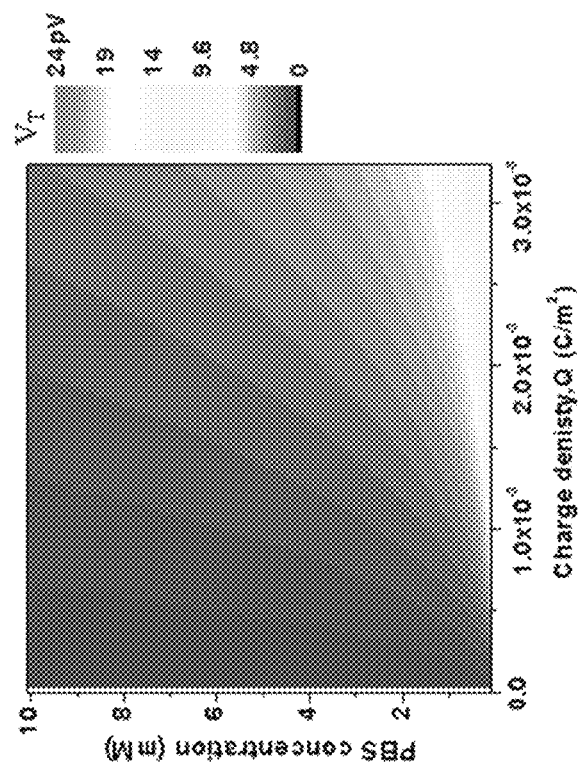

Equations 3~11 completely determines how the ionic concentration and charge density affect the potential coupling efficiency and the induced gate potential VT. FIGS. 20A-20B show $V_T$ induced by Q (charge density) at various Phosphate-buffered saline (PBS) buffer concentrations for $A_{ratio}$=0.5, $C_{ratio}$=0.01 and x=200 when Q is atop of sensing electrode and when Q is located at a region outside electrode, respectively. The ion concentration affects $C_{dl}$, so that in the case of high ion concentration, the induced gate potential is very small when $A_{ext}$=$A_{pro}$=0.5 cm², d=10 nm, $C_T/C_{Dry}$=0.01, x=200. However, $V_T$ increases times when ionic strength changes from 10 mM to 1 mM, hence most studies using SiNW FET biosensor used PBS buffer with approximate 1 mM concentration. The type B equivalent circuit at various PBS concentrations and charge densities is also simulated; the charge induced gate potential is about 9 order smaller than that of the type A configuration as shown in FIG. 20B. Moreover, the binding charge outside the sensing electrode hardly affects VT. Therefore, a proper design of the sensing electrode can eliminate the influence of charge binding outside the sensing electrode while maintaining a high potential coupling efficiency.

As such, in conditions of 1×PBS (ionic strength ~150 mM), x>>10 and $C_{Dry} \gg C_T$ (1000 times), the potential coupling efficiency η is too small to detect.

Moreover, in conditions of 0.1×PBS (ionic strength ~15 mM), x>>10 and $C_{Dry} \gg C_T$ (1000 times), the potential coupling efficiency η is <10%.

Preferably, in conditions of 0.01×PBS (ionic strength ~1.5 mM), x>>10 and $C_{Dry} \gg C_T$ (1000 times), the potential coupling efficiency η is >99%.

Figure 21B:
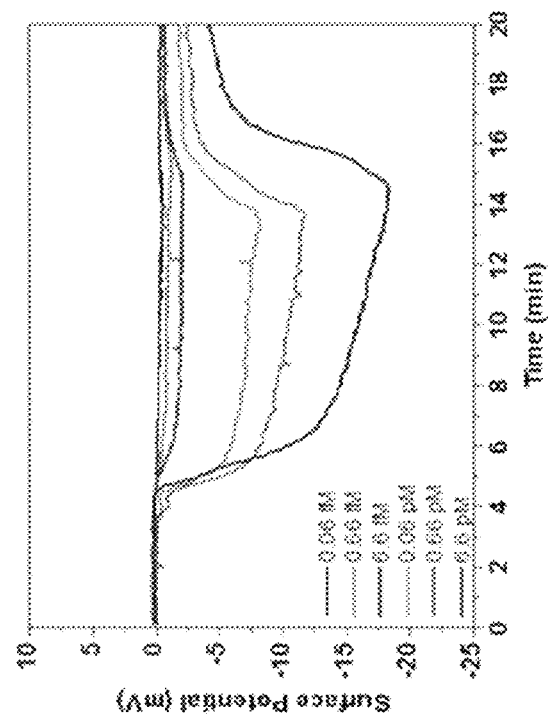
FIG. 21B shows a real-time BoNTs sensing with a BoNT Ab modified sensing electrode.
Figure 21A:
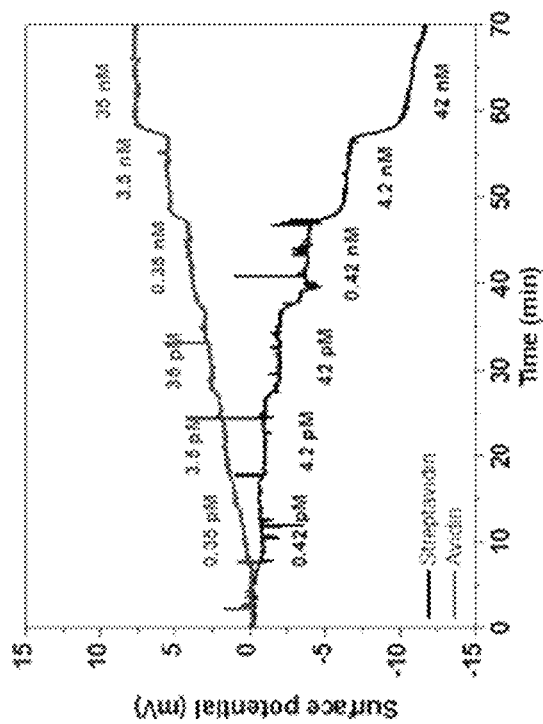
FIG. 21A shows a real-time streptavidin/avidin sensing with a biotin modified sensing electrode.

FIG. 21A shows a real-time streptavidin/avidin sensing with a biotin modified sensing electrode; and FIG. 21B shows a real-time BoNTs sensing with a BoNT Ab modified sensing electrode. The area of sensing electrode $A_{ox1}$ is 7.6 mm², the capacitor of sensing electrode, $C_{Dry}$, is 20 nF, the gate capacitor, $C_T$, is 3 pF, and x=200. The subthreshold swing of NW FET is ~62 mV/dec.

It should be noted that the present disclosure may further include a preamplifier module and a postamplifier module. The sensing chip is disposed on the preamplifier module via a plurality of pogo pins. The preamplifier module is electrically connected to the postamplifier module. In addition, the postamplifier may include a digital-to-analog converter (DAC), a analog-to-digital converter (ADC), a micro controller, an operational amplifier (opamp), a reference electrode bias terminal, a USB terminal and a power supply terminal.

It is also worth mentioning that the present disclosure may further include a mechanical sensing system, as shown in FIG. 22. The mechanical sensing system may have a slider 30, a guide pipette 32, a pipette slide cover 34 and a metal chassis 36. The slider 30 is used for alignment and contacts between the sensing chip and a plurality of pogo pins. A pipette tip of the guide pipette 32 is fastened at the same level atop the sensing electrode. The pipette slide cover 34 is used to avoid light interference. Moreover, the metal chassis is used to avoid electromagnetic interference.

In summary, according to the above preferred embodiments of the present disclosure, the biological sensing system of the present disclosure includes a nanowire FET and a sensing chip. The nanowire FET may be a JL transistor, a IM transistor or a gated nanowire diode. A gate terminal of the nanowire FET surrounds a gate of a silicon nanowire or a gate of a silicon nanobelt, the diameter of the gate-all-around silicon nanowire is less than 20 nm and the channel thickness of the gate-all-around silicon nanobelt is less than 15 nm. A sensing electrode of the sensing chip is coupled to the gate terminal of the nanowire FET. An area ratio of an electrode area of the sensing electrode to a total chip area, a thickness ratio of an oxide thickness to a bulk oxide dielectric film thickness of the sensing electrode and a capacitance ratio of an electrode capacitor of the sensing electrode to a gate capacitor of the gate-all-around silicon nanowire or a gate capacitor of gate-all-around silicon nanobelt are optimized by means of an equivalent circuit to obtain optimized potential coupling efficiency.

The above preferred embodiments describe the principle and effect of the present disclosure, but are not limited to the present disclosure. It will be apparent to a person ordinarily skilled in the art that various modifications and variations can be made to the disclosed embodiments. It is intended that the specification and examples be considered as exemplary embodiment only, with a true scope of the disclosure being indicated by the following claims and their equivalents.

Although the present disclosure has been described with reference to the preferred exemplary embodiments thereof, it is apparent to those skilled in the art that a variety of modifications and changes may be made without departing from the scope of the present disclosure which is intended to be defined by the appended claims.

What is claimed is:

1. A biological sensing system, comprising:
 a nanowire field-effect transistor, having a source terminal, a drain terminal and a gate terminal, the gate terminal being electrically connected to and surrounds a gate of a silicon nanowire, of which a diameter is less than 20 nm, or being electrically connected to a gate of a junctionless silicon nanobelt, of which a channel thickness is less than 15 nm;
 a sensing chip having an extended gate, the extended gate having a sensing electrode, the sensing electrode being coupled to the gate terminal of the nanowire field-effect transistor; and
 a preamplifier module, on which the sensing chip is disposed via a plurality of pogo pins, wherein
 a thickness ratio of an oxide thickness of the sensing electrode to a bulk oxide dielectric film thickness of the extended gate is at least 10, and
 a capacitance ratio of a gate capacitor of the silicon nanowire or a gate capacitor of the silicon nanobelt to an electrode capacitor of the sensing electrode is less than 0.1.

2. The biological sensing system according to claim 1, wherein the sensing chip further comprises a fluid well and a printed circuit board (PCB), wherein the fluid well is disposed on the sensing electrode, and the sensing electrode is electrically connected to the PCB.

3. The biological sensing system according to claim 1, wherein the sensing chip is disposable.

4. The biological sensing system according to claim 1, further comprising a mechanical sensing system, having a slider, a guide pipette, a pipette slide cover and a metal chassis, wherein
 the slider is used for alignment and contacts between the sensing chip and the plurality of pogo pins;
 a pipette tip of the guide pipette is fastened at the same level atop the sensing electrode;
 the pipette slide cover is used to avoid light interference; and
 the metal chassis is used to avoid electromagnetic interference.

5. The biological sensing system according to claim 1, wherein the nanowire field-effect transistor is an inversion mode nanowire field-effect transistor, the silicon nanowire is an inversion mode silicon nanowire, and the silicon nanobelt is an inversion mode silicon nanobelt.

6. The biological sensing system according to claim 5, wherein the sensing chip further comprises a fluid well and a printed circuit board (PCB),
 wherein the fluid well is disposed on the sensing electrode, and the sensing electrode is electrically connected the PCB.

7. The biological sensing system according to claim 5, wherein the sensing chip is disposable.

8. The biological sensing system according to claim 5, further comprising a mechanical sensing system, having a slider, a guide pipette, a pipette slide cover and a metal chassis, wherein
 the slider is used for alignment and contacts between the sensing chip and the plurality of pogo pins;
 a pipette tip of the guide pipette is fastened at the same level atop the sensing electrode;
 the pipette slide cover is used to avoid light interference; and
 the metal chassis is used to avoid electromagnetic interference.

9. A biological sensing system, comprising:
 a gated nanowire diode, having a source terminal, a drain terminal and a gate terminal, the gate terminal being electrically connected to and surrounds a gate of a silicon nanowire, of which a diameter is less than 20 nm, or being electrically connected to a gate of a silicon nanobelt, of which a channel thickness is less than 15 nm;
 a sensing chip having an extended gate, the extended gate including a sensing electrode, the sensing electrode being coupled to the gate terminal of the gated nanowire diode; and
 a preamplifier module, on which the sensing chip is disposed via a plurality of pogo pins, wherein
 a thickness ratio of an oxide thickness of the sensing electrode to a bulk oxide dielectric film thickness of the extended gate is at least 10, and a capacitance ratio of a gate capacitor of the silicon nanowire or a gate capacitor of the silicon nanobelt to an electrode capacitor of the sensing electrode is less than 0.1.

10. The biological sensing system according to claim 9, wherein the sensing chip further comprises a fluid well and a printed circuit board (PCB), wherein the fluid well is disposed on the sensing electrode, and the sensing electrode is electrically connected the PCB.

11. The biological sensing system according to claim 9, wherein the sensing chip is disposable.

12. The biological sensing system according to claim 9, further comprising a mechanical sensing system, having a slider, a guide pipette, a pipette slide cover and a metal chassis, wherein
- the slider is used for alignment and contacts between the sensing chip and the plurality of pogo pins;
- a pipette tip of the guide pipette is fastened at the same level atop the sensing electrode;
- the pipette slide cover is used to avoid light interference; and
- the metal chassis is used to avoid electromagnetic interference.

13. The biological sensing system according to claim 1, wherein the nanowire field-effect transistor is a junctionless nanowire field-effect transistor, the silicon nanowire is a junctionless silicon nanowire, and the silicon nanobelt is a junctionless silicon nanobelt.

14. The biological sensing system according to claim 13, wherein a reference electrode is immersed in a phosphate-buffered saline (PBS) buffer solution at a fluid well, the reference electrode bias being applied through a reference electrode to manipulate the junctionless nanowire field-effect transistor through the PBS buffer solution.

15. The biological sensing system according to claim 5, wherein a reference electrode is immersed in a phosphate-buffered saline (PBS) buffer solution at a fluid well, a reference electrode bias being applied through a reference electrode to manipulate the inversion mode nanowire field-effect transistor through the PBS buffer solution.

16. The biological sensing system according to claim 9, wherein a reference electrode is immersed in phosphate-buffered saline (PBS) buffer solution at a fluid well, the reference electrode bias being applied through a reference electrode to manipulate the gated nanowire diode through the PBS buffer solution.

* * * * *